United States Patent [19]

Pinza et al.

[11] Patent Number: 4,629,797
[45] Date of Patent: Dec. 16, 1986

[54] PROCESS FOR THE PREPARATION OF PYRROLIDONE DERIVATIVES

[75] Inventors: Mario Pinza; Ugo C. Pfeiffer, both of Milan, Italy

[73] Assignee: I.S.F. Societa per Azioni, Milan, Italy

[21] Appl. No.: 718,242

[22] Filed: Mar. 29, 1985

[30] Foreign Application Priority Data

Apr. 2, 1984 [IT] Italy .............................. 20358 A/84

[51] Int. Cl.$^4$ ......................................... C07D 207/273
[52] U.S. Cl. ..................................... 548/544; 564/201
[58] Field of Search ......................................... 548/544

[56] References Cited

U.S. PATENT DOCUMENTS 4,124,594 11/1978 Monguzzi et al. .................... 548/544
4,173,569 11/1979 Banfi et al. ........................... 548/544

OTHER PUBLICATIONS

Tabei et al, *Heterocycles* 14:1779-1784(1980).
Pifferi et al, *Il Farmaco* (Ed. Sc.) 32:602-613(1977).

*Primary Examiner*—Richard L. Raymond
*Assistant Examiner*—D. B. Springer

*Attorney, Agent, or Firm*—Joan S. Keps; Stuart R. Suter; Alan D. Lourie

[57] ABSTRACT

A process for preparing compounds (1)

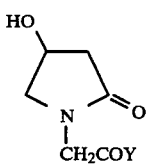

where Y is $NR^1R^2$ or OR, $R^1$ and $R^2$ are hydrogen or $C_{1-3}$ alkyl, and R is $C_{1-3}$ alkyl, which comprises protecting the hydroxy group of a compound (2)

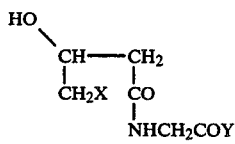

cyclising the product under basic conditions and removing the protecting group.

8 Claims, No Drawings

PROCESS FOR THE PREPARATION OF PYRROLIDONE DERIVATIVES

The present invention concerns a process for the preparation of pyrrolidone derivatives and intermediates for such compounds. More particularly, the present invention concerns a process and intermediates for preparing 4-hydroxy-2-oxo-1-pyrrolidineacetamide (oxiracetam) and its N-derivatives which are useful psychotropic compounds which restore cognitive function in animals and man which have been damaged as a result of various pathologies.

Several processes exist at present for preparing oxiracetam and its analogues. One process which starts from gamma-amino-beta-hydroxybutyric acid is described in the British Pat. No. 1588074, and another process which starts from a protected glycinamide and an epoxybutanoate is described in Italian Patent Application No. 19802A/84. The aim of the present invention is to provide an alternative process for the preparation of oxiracetam and its N-alkyl analogues using different starting materials which are commercially available at economically interesting costs.

According to one aspect of the present invention we provide a process for preparing 4-hydroxy-2-oxo-1-pyrrolidine derivatives of structure (1):

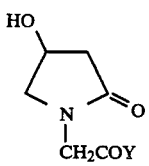  (1)

in which Y is $NR^1R^2$ or OR, where $R^1$ and $R^2$, which can be the same or different, are hydrogen or $C_{1-3}$ alkyl and R is $C_{1-3}$ alkyl, which comprises protecting the hydroxy group of a compound of structure (2):

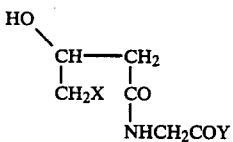  (2)

wherein X is chloro or bromo, and Y is $NR^1R^2$ or OR where $R^1$ and $R^2$, which can be the same or different, are hydrogen or $C_{1-3}$ alkyl, and R is $C_{1-3}$ alkyl, with a protecting group which is stable under basic conditions and removeable under acidic conditions, to give a compound of structure (3)

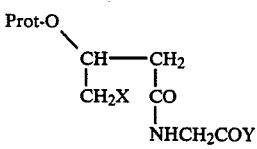  (3)

in which Prot is a hydroxy-protecting group which is stable under basic conditions and removeable under acidic conditions, cyclising the compound of structure (3) in the presence of a strong non-nucleophilic base formed from an alkali metal to give a compound of structure (4)

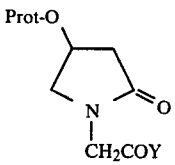  (4)

in which Prot is a hydroxy-protecting group which is stable under basic conditions and removeable under acidic conditions, and Y is $-NR^1R^2$ or OR, removing the group Prot under acidic conditions, and optionally reacting the products in which Y is OR with an amine of formula $HNR^1R^2$.

Hydroxy-protecting groups which are stable under basic conditions and removeable under acidic conditions are generally known in the art and are described in standard textbooks for example various ether groups described at p.14 et seq. in 'Protective Groups in Organic Chemistry' by T. W. Greene (John Wiley 1981). The protecting group chosen should not be too sterically bulky to prevent the cyclisation reaction. We have found that the compound of structure (3) in which Prot is trimethylsilyl cannot be cyclised easily and we believe that this is probably due to unfavourable steric hinderance caused by the protecting group shielding carbon atoms adjacent to the carbinol group from nucleophilic attack. Preferably Prot is tetrahydropyranyl, or α-ethoxyethyl, particularly preferably tetrahydropyranyl.

Tetrahydropyranyl derivatives are prepared by reaction with dihydropyran and preferably this reaction is performed at room temperature in a solvent selected from for example methylene chloride, chloroform, tetrahydrofuran, toluene, benzene etc. and in the presence of an acid catalyst, preferably pyridine paratoluenesulphonate (PPTS). Examples of other acid catalysts are p-toluenesulphonic acid, sulphuric acid, phosphoryl chloride and polyphosphoric acid. When PPTS is used the amount of PPTS used is preferably 10% with respect to compound (2) on a molar basis. Preferably about 1.0 to 1.5 molar equivalents of dihydropyran are used.

Preferably Y is $NR^1R^2$ and preferably $R^1$ and $R^2$ are both hydrogen.

When Y is OR preferably it is $-OC_2H_5$.

Preferably the strong non-nucleophilic base is sodium hydride or potassium t-butoxide. Preferably the cyclisation reaction is carried out at a temperature of $-10°$ C. to $+30°$ C., preferably at about $0°$ C., in a suitable solvent for example tetrahydrofran (THF), toluene, methylene chloride ($CH_2Cl_2$) or dioxane.

The alkyl 4-hydroxy-2-oxo-1-pyrrolidine derivatives (4) can be deprotected by heating, e.g. at $20°-70°$ C. in a suitable solvent, for example ethanol, methanol, isopropanol or water, in the presence of an acid catalyst. Preferably the acid catalyst is pyridine p-toluenesulphonate (PPTS), p-toluenesulphonic acid, hydrochloric acid or sulphuric acid. Particularly preferably the acid catalyst is PPTS.

The alkyl 4-hydroxy-2-oxo-1-pyrrolidineacetates ((4) Y=OR) can be converted to compounds of Structure (4) in which Y is $NR^1R^2$ by aminolysis with an amine $HNR^1R^2$ in a solvent such as water, methanol or ethanol at a temperature between $-10°$ and $+50°$ C.

The compounds of structures (2) and (3) are novel and form an important aspect of this invention.

The compounds of structure (2) can be prepared by reducing a compound of structure (6)

XCH$_2$CCH$_2$CONHCH$_2$COY  (6)

Suitable reducing agents are those of the hydride class. Preferably the reducing agent is sodium borohydride (NaBH$_4$). Preferably the reduction is performed at $-10°$ to $+30°$ C., preferably at about 0° C, in a solvent selected for example from dimethoxyethane, tetrahydrofuran, ethyl ether, 2-methoxyethanol, ethanol, methanol, isopropanol or water.

The compounds of structure (6) can be prepared by reacting gamma-bromoacetoacetyl bromide or gamma-chloroacetoacetyl chloride with a glycine derivative of structure (7)

NH$_2$CH$_2$COY  (7)

where Y is NR$^1$R$^2$ or OR where R is C$_{1-3}$ alkyl.

Preferably the reaction is performed at low temperatures of from $-78°$ C. to $+10°$ C., preferably $-50°$ to $-20°$ C., under anhydrous conditions in a solvent selected from methylene chloride, chloroform, tetrahydrofuran or toluene. Preferably the bromoacetoacetyl bromide or the chloroacetoacetyl chloride are prepared in situ by reacting diketene with bromine or chlorine. Preferably the halogen is added to diketene dissolved in a solvent, either as a solution or by bubbling it as a gas, and then the glycine ester or amide of structure (7) is added. When a glycine ester or amide is used preferably it is liberated in situ from one of its salts, e.g. the hydrochloride by the addition of an inorganic or organic base. Preferably an equimolar ratio of reagents is used, although it is possible to use an excess of one or the other.

The compounds of structure (6) are novel and form an important aspect of this invention.

It will be appreciated that the compounds of structures (1), (2), (3) and (4) have at least one chiral carbon atom and, for example, when Prot is tetrahydropyranyl compounds of structures (3) and (4) have two chiral carbon atoms. This invention relates to racemic mixtures and to the resolved optical isomers and diasteroisomeric mixtures of the compounds described.

The examples that follow illustrate the invention but do not limit it.

EXAMPLE 1

Methyl 2-(4-bromo-3-oxobutanamido)acetate 4.8 ml Diketene are dissolved in 30 ml methylene chloride. The solution is cooled to $-50°$ C. and a solution of 3.24 ml bromine dissolved in 20 ml methylene chloride is added dropwise over 30 min. The mixture is left stirring for 2 h at ambient temperature. At $-40°$ is added, all at once, an intimate mixture of 20 g finely ground Na$_2$CO$_3$ and 7.9 g glycine methyl ester hydrochloride. Stirring is continued for 90 min, allowing the mixture to return to ambient temperature. The salt is filtered quickly, the filtrate is concentrated in vacuo at ambient temperature. The residual oil is purified by chromatography on silica, eluting with ethyl acetate. The desired compound is obtained as a white powder, m.p. 76°–77° C.

EXAMPLE 2

Methyl 2-(4-bromo-3-hydroxybutanamido)acetate 1.5g Methyl 2-(4-bromo-3-oxobutanamido)acetate is dissolved in 15 ml dimethoxyethane. The solution is cooled to 0° C. and 60 mg NaBH$_4$ is added. After 5 min, the solvent is evaporated in vacuo and the residue is chromatographed on silica, eluting with ethyl acetate. The title compound is obtained as a white powder, m.p. 60°–61° C.

EXAMPLE 3

Methyl 2-(4-bromo-3-hydroxybutanamido)acetate 0.76 ml Diketene is dissolved in 3.5 ml methylene chloride. The solution is cooled to $-30°$ C. and a solution of 0.5 ml bromine in 3.5 ml methylene chloride is added slowly dropwise, after which stirring is continued at $-30°$ C. for 10 mins. This solution is added quickly dropwise to a solution of glycine methyl ester prepared by suspending 1.25 g glycine methyl ester hydrochloride in 20 ml methylene chloride containing 2.8 ml triethylamine, stirring for 30 min and cooling to $-30°$ C. The temperature is allowed to return to ambient with continued stirring. After filtering, and evaporating in vacuo at ambient temperature, the oil remaining is dissolved in 20 ml ethanol, cooled to 0° C. and treated with 100 mg NaBH$_4$. After 5 min the excess hydride is destroyed with dilute acid, the ethanol is evaporated and the residue taken up with ethyl acetate; the solution is washed with brine, dried, evaporated, and purified by chromatography on silica, eluting with ethyl acetate. The title compound is obtained as a white powder, m.p. 60°–61° C.

EXAMPLE 4

Ethyl 2-(4-bromo-3-hydroxybutanamido)acetate

Proceed as described above, using 1.4 g glycine ethyl ester hydrochloride. A white powder is obtained, m.p. 59°–61° C.

EXAMPLE 5

Methyl 2-(4-bromo-3-(tetrahydropyran-2-yloxy)butanamido)acetate

To a solution of 300 mg methyl 2-(4-bromo-3-hydroxybutanamido)acetate in 50 ml methylene chloride are added 30 mg pyridinium p-toluenesulphonate and 1 ml dihydropyran. After stirring at ambient temperature for 20 h, the solvent is evaporated in vacuo and the residue chromatographed on silica, eluting with ether. A colourless oil is obtained in 92% yield, Rf 0.33 (silica gel plates, thickness 0.25, eluent diethyl ether).

EXAMPLE 6

Ethyl 2-(4-bromo-3-(tetrahydropyran-2-yloxy) butanamido)-acetate

To a solution of 1 g ethyl 2-(4-bromo-3-hydroxybutanamido)acetate in 30 ml methylene chloride are added 100 mg pyridinium p-toluenesulphonate and 1 ml dihydropyran. Stirring is continued for 3 h at ambient temperature, the solvent is evaporated in vacuo and the residue chromatographed on silica, eluting with ether. A pale straw-coloured oil is obtained in 91% yield, Rf 0.5 (silica gel plates, thickness 0.25 mm eluent ethyl acetate).

EXAMPLE 7

Ethyl 2-(4-chloro-3-oxobutanamido)acetate 5.08 ml diketene are dissolved in 40 ml CH$_2$Cl$_2$. The solution is cooled to $-30°$ C. and chlorine is passed through it for 1 h. The solution is then added rapidly dropwise to a solution of glycine ethyl ester prepared by suspending 9.30 g glycine ethyl ester hydrochloride in 160 ml methylene chloride containing 18.6 ml triethylamine, the mixture is stirred for 30 min and cooled to $-30°$ C. Stirring is continued for 30 min, the solvent is evaporated in vacuo, and the residue taken up in ethyl acetate. The salts are filtered off, the solvent is evaporated and the residue chromatographed on silica, eluting with ethyl acetate. The compound is obtained as a white powder, m.p. 96°–7° C.

EXAMPLE 8

Ethyl 2-(4-chloro-3-hydroxybutanamido)acetate 5.08 ml diketene are dissolved in 40 ml CH$_2$Cl$_2$. The solution is cooled to $-30°$ C. and chlorine is passed through for 90 min. The solution is then added rapidly dropwise to a solution of glycine ethyl ester in 160 ml CH$_2$Cl$_2$ prepared as in the preceding example. After stirring for 30 min, the solvent is evaporated in vacuo, the residue is taken up in ethyl acetate and the salts filtered off. The solvent is evaporated, the oily residue is dissolved in 150 ml ethanol, cooled in ice, and 1.26 g NaBH$_4$ is added in portions. After 30 min a few drops of dilute hydrochloric acid are added, the solvent is evaporated, the residue is taken up in ethyl acetate, washed with brine and dried. The solvent is evaporated and the residue chromatographed on silica, eluting with ethyl acetate. The compound is obtained as a white powder, m.p. 53°–4° C.

EXAMPLE 9

Ethyl 2-(4-chloro-3-(tetrahydropyran-2-yloxy)butanamido)acetate 1 g Ethyl 2-(4-chloro-3-hydroxybutanamido)acetate is dissolved in 10 ml CH$_2$Cl$_2$. 100 mg pyridine p-toluenesulphonate and 0.5 ml dihydropyran are added. The mixture is stirred for 7 h. The solvent is evaporated and the residue chromatographed, eluting with ethyl acetate. A colourless oil is obtained, Rf 0.5 (silica gel plates, thickness 0.25 mm, eluent ethyl acetate).

EXAMPLE 10

Ethyl 2-oxo-4-(tetrahydropyran-2-yl)-1-pyrrolidineacetate 150 mg NaH are suspended in 20 ml tetrahydrofuran, and the mixture is cooled in ice. To this suspension is added a solution of 2.5 g ethyl 2-(4-bromo-3-(tetrahydropyran-2-yloxy)butanamido)acetate in 30 ml tetrahydrofuran. The mixture is stirred 40 min, then poured with stirring into a solution of 1 ml acetic acid in 10 ml water at 0° C. The solution is extracted with ether, the organic phase is washed with a saturated solution of NaHCO$_3$, then washed with brine, dried and evaporated. The crude oil obtained is purified by chromatography on silica, eluting with ethyl acetate. A colourless oil is obtained, Rf 0.32 (silica gel plates, thickness 0.25 mm, eluent ethyl acetate).

EXAMPLE 11

Ethyl 2-oxo-4-(tetrahydropyran-2-yl)-1-pyrrolidineacetate

Proceeding as described previously, and using 2.24 g ethyl 2-(4-chloro-3-(tetrahydropyran-2-yloxy)-butanamido)acetate, a colourless oil is obtained, Rf 0.32 (silica gel plates, thickness 0.25 mm, eluent ethyl acetate).

EXAMPLE 12

Ethyl 4-hydroxy-2-oxo-1-pyrrolidineacetate

A solution of 0.16 g ethyl 2-oxo-4-(tetrahydropyran-2-yl)-1-pyrrolidineacetate is dissolved in 5 ml ethanol containing 16 mg pyridinium p-toluenesulphonate. The mixture is heated 4 h at 35°, the ethanol is evaporated and the residue chromatographed on silica. The title compound is obtained as a colourless oil in 62% yield.

EXAMPLE 13

4-Hydroxy-2-oxo-1-pyrrolidineacetamide

A solution of 7.1 g ethyl 4-hydroxy-2-oxo-1-pyrrolidineacetate obtained in Example 12, in 7.1 ml ammonia solution (d$_{25}$=0.90) is stirred at ambient temperature for 15 h. It is then diluted with 140 ml acetone and the mixture is stirred at ambient temperature until the gum that precipitates solidifies into white crystals. On filtering in vacuo and drying, 4-hydroxy-2-oxo-1-pyrrolidineacetamide is obtained, m.p. 160°–162° C.

EXAMPLE 14

Substitution of glycineamide hydrochloride for glycine methyl ester hydrochloride in the procedure of Example 1 gives 2-(4-bromo-3-oxobutanamido)acetamide and successive reaction of this with sodium borohydride, dihydropyran, and sodium hydride according to the procedures of Examples 2, 5 and 10 gives 2-(4-bromo-3-hydroxybutanamido)acetamide, 2-(4-bromo-3-(tetrahydropyran-2-yloxy)butanamido)acetamide and 2-oxo-4-(tetrahydropyran-2-yl)-1-pyrrolidineacetamide, respectively. Deprotection of the latter compound with pyridinium p-toluenesulphonate in ethanol gives 4-hydroxy-2-oxo-1-pyrrolidineacetamide.

What is claimed is:

1. A process for preparing a compound of structure (1):

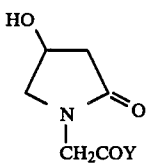

(1)

in which Y is NR$^1$R$^2$ or OR where R$^1$ and R$^2$, which can be the same or different, are hydrogen or C$_{1-3}$ alkyl and R is C$_{1-3}$ alkyl, which comprises protecting the hydroxy group of a compound of structure (2):

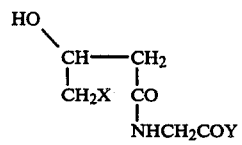

(2)

wherein X is chloro or bromo and Y is as defined above with a protecting group which is stable under basic conditions and removeable under acidic conditions, to give a compound of structure (3)

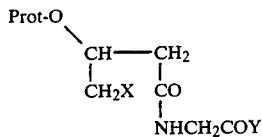 (3)

in which Prot is a hydroxy-protecting group which is stable under basic conditions and removeable under acidic conditions, cyclising the compound of structure (3) in the presence of a strong non-nucleophilic base formed from an alkali metal to give a compound of structure (4)

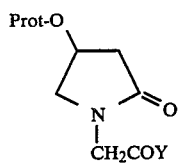 (4)

in which Prot is a hydroxy-protecting group which is stable under basic conditions and removeable under acidic conditions and Y is -$NR^1R^2$ or OR, removing the group Prot under acidic conditions, and optionally reacting the product in which Y is OR with an amine of formula $HNR^1R^2$.

2. A process according to claim 1 in which the strong base is sodium hydride or potassium t-butoxide.

3. A process according to claim 1 in which Prot is tetrahydropyranyl or α-ethoxyethyl.

4. A process according to any one of claims 1 to 3 in which in all the compounds of structures (1), (2), (3) and (4) Y is $NR^1R^2$ and $R^1$ and $R^2$ are both hydrogen.

5. A process according to any one of claims 1 to 3 in which Y in all of the compounds of structures (1), (2), (3) and (4) is $-OC_2H_5$.

6. A process according to any one of claims 1 to 3 in which the compound of structure (2) is prepared by reducing a compound of structure (6)

 (6)

in which Y is $NR^1R^2$ or OR where $R^1$ and $R^2$, which can be the same or different, are hydrogen or $C_{1-3}$ alkyl and R is $C_{1-3}$ alkyl.

7. A process according to claim 6 in which the compound of structure (6) is prepared by reacting gamma-bromoacetoacetyl bromide or gamma-chloroacetoacetyl chloride with a glycine derivative of structure (7)

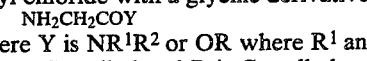 (7)

where Y is $NR^1R^2$ or OR where $R^1$ and $R^2$ are hydrogen or $C_{1-3}$ alkyl and R is $C_{1-3}$ alkyl.

8. A process according to claim 7 in which the gamma-bromoacetoacetyl bromide or the gamma-chloroacetoacetyl chloride is prepared in situ by reacting diketene with bromine or chlorine.

* * * * *